United States Patent
Alkayali

(10) Patent No.: US 11,732,015 B2
(45) Date of Patent: Aug. 22, 2023

(54) METHOD OF DRYING JELLYFISH MATTER

(71) Applicant: Ahmad Alkayali, Pauma Valley, CA (US)

(72) Inventor: Ahmad Alkayali, Pauma Valley, CA (US)

( * ) Notice: Subject to any disclaimer, the term of this patent is extended or adjusted under 35 U.S.C. 154(b) by 426 days.

(21) Appl. No.: 16/219,813

(22) Filed: Dec. 13, 2018

(65) Prior Publication Data

US 2020/0190152 A1   Jun. 18, 2020

(51) Int. Cl.
| | | |
|---|---|---|
| *C07K 14/435* | (2006.01) | |
| *C07K 1/14* | (2006.01) | |
| *A23J 1/04* | (2006.01) | |
| *A01N 1/02* | (2006.01) | |

(52) U.S. Cl.
CPC ........... *C07K 14/43595* (2013.01); *A23J 1/04* (2013.01); *C07K 1/14* (2013.01); *A01N 1/0221* (2013.01)

(58) Field of Classification Search
CPC ...... A23J 3/04; A23J 1/04; A23J 3/342; A23L 13/20; A23L 19/01; A23L 29/284; A23L 33/18; A01N 1/0221; C07K 14/43595; A23B 4/037
See application file for complete search history.

(56) References Cited

U.S. PATENT DOCUMENTS

| | | | |
|---|---|---|---|
| 2005/0175592 A1* | 8/2005 | Wu | A61K 35/761 424/93.2 |
| 2008/0260915 A1 | 10/2008 | Alkayali | |
| 2018/0237498 A1* | 8/2018 | Alkayali | A61Q 19/00 |

OTHER PUBLICATIONS

Chan, Vicky "Jellyfish—for Brain & HEart Health" NourishU, archived May 30, 2016 <URL: chinesemedicineliving.com/nutrition/recipes/jellyfish-for-brain-heart-health/>, 9 pages. (Year: 2016).*
Labconco "A Guide To Freeze Drying for the Laboratory" Labconco Corporation, 2008, 12 pages. (Year: 2008).*

* cited by examiner

*Primary Examiner* — Aaron J Kosar
(74) *Attorney, Agent, or Firm* — John R. Ross; John R. Ross, III

(57) ABSTRACT

A method for drying moist jellyfish matter is provided. Jellyfish matter undergoes a controlled drying process until the jellyfish matter comprises a dried flake or mass.

4 Claims, 4 Drawing Sheets

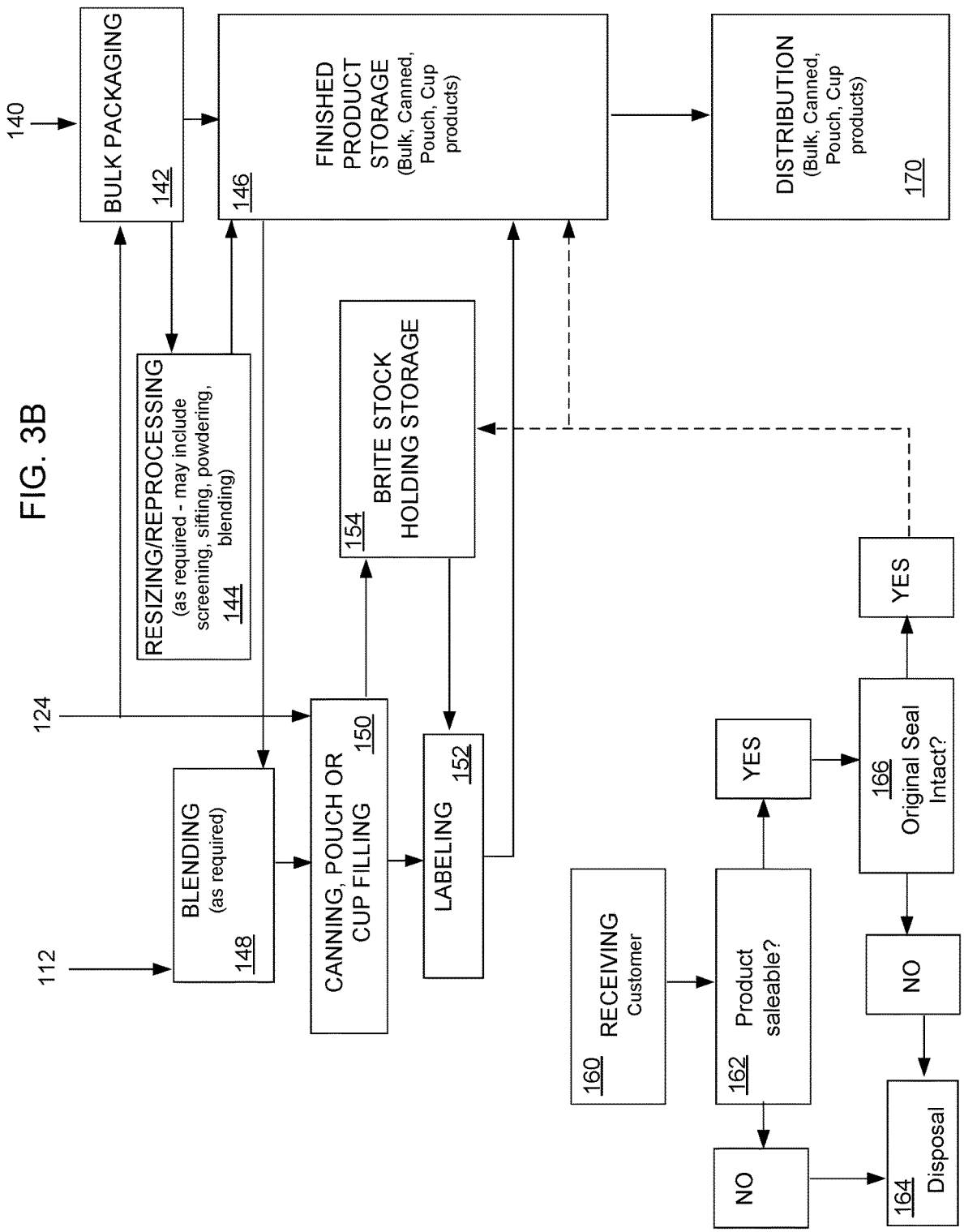

METHOD OF DRYING JELLYFISH MATTER

BACKGROUND OF THE INVENTION

1. Field of Invention

The present invention relates to a method of drying moist material.

2. Description of Related Art

Collagen is a complex structural protein which provides strength and flexibility to skin, hair, and nails. Collagen is a major component of muscles, tendons, cartilage, ligaments, joints, and blood vessels. Hydrolyzed coastal jellyfish collagen is extracted from two species of edible jellyfish. The two species, *Stomolophus meleagris* and *Acromitus hardenbergi,* contain the highest amount of amino acid collagen types I, II, and V. Type I is primarily found in skin and tendons while type II is primarily found in articular cartilage. Cartilage is unusual in that it has a high proportion of glycine and proline residues. Specifically, 4-hydroxyproline and 5-hydroxylysine are found in very few other protein sources, adding benefit to the intake of exogenous collagen.

Several research studies on jellyfish collagen have been conducted in vivo showing positive health benefits such as improved brain function, reversal of photo-aging, fatigue reduction, arthritis prevention, and reduced cellular oxidation. Further, collagen helps to stimulate the immune system and neurological activities.

Based on the foregoing, there is a need for a simple process to remove moisture from edible jellyfish matter that may be utilized as a supplement, prophylactic, or treatment for a wide range of conditions. The composition should be available for use in a variety of forms for topical or oral administration.

SUMMARY OF THE INVENTION

A method for drying jellyfish material. In an embodiment, moist jellyfish material is introduced at one end of an apparatus in a heat-transfer relation with a heated water bath. In an embodiment, a sheet is provided to prohibit moisture from transferring from the water bath to the moist jellyfish material.

In an embodiment, the moist jellyfish material is also exposed to heat transfer and moisture-loss relationship with a warm and humidity-controlled air flow stream. The jellyfish material is provided said heat transfer and moisture-loss relationship until the material is sufficiently dried.

In an embodiment, the moist jellyfish material undergoes lyophilization in a freeze-drying apparatus. In the embodiment, pretreated jellyfish material is placed into a freeze-drying apparatus wherein the temperature is lowered below the eutectic point of the material. A vacuum is applied to the apparatus and the heat is raised such that the water sublimates from the jellyfish material.

The foregoing, and other features and advantages of the invention, will be apparent from the following, more particular description of the preferred embodiments of the invention, the accompanying drawings, and the claims.

BRIEF DESCRIPTION OF THE DRAWINGS

For a more complete understanding of the present invention, the objects and advantages thereof, reference is now made to the ensuing descriptions taken in connection with the accompanying drawings briefly described as follows.

FIG. 3B is a diagram depicting the manufacturing of dried jellyfish collagen, according to an embodiment of the present invention.

DETAILED DESCRIPTION OF PREFERRED EMBODIMENTS

Figure 1:
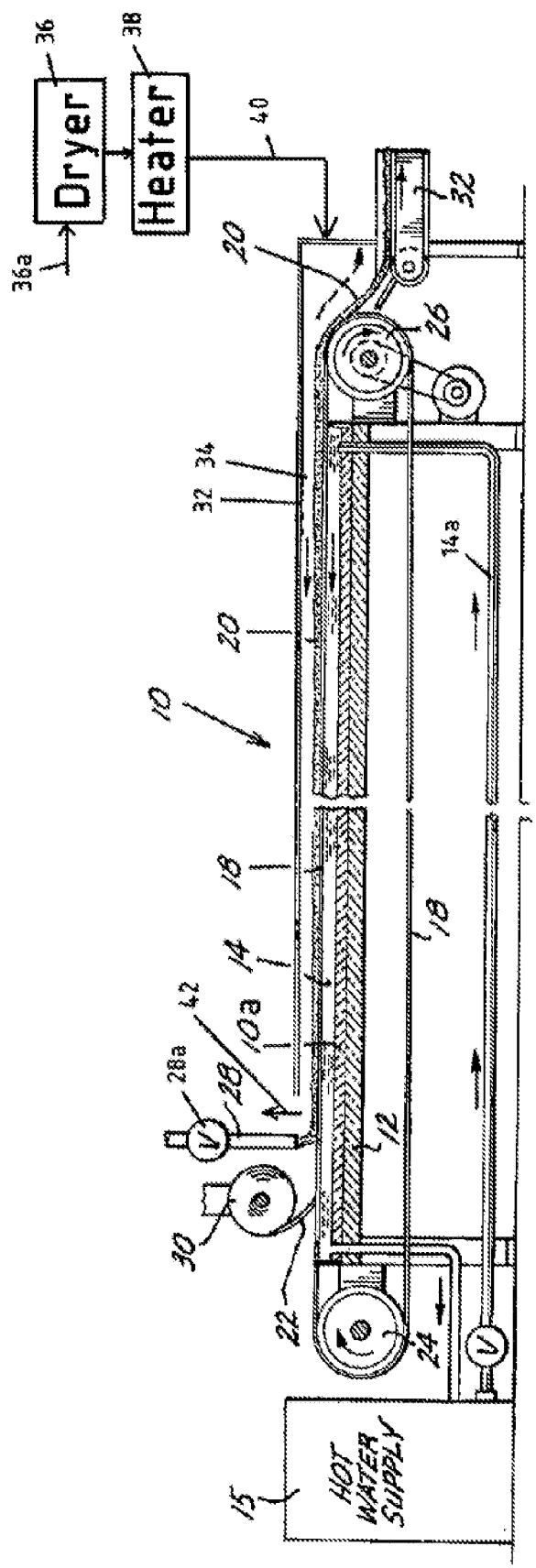
FIG. 1 is a side elevation view of a drying apparatus, according to an embodiment of the present invention.

Preferred embodiments of the present invention and their advantages may be understood by referring to FIG. 1-3B, wherein like reference numerals refer to like elements.

Figure 2:
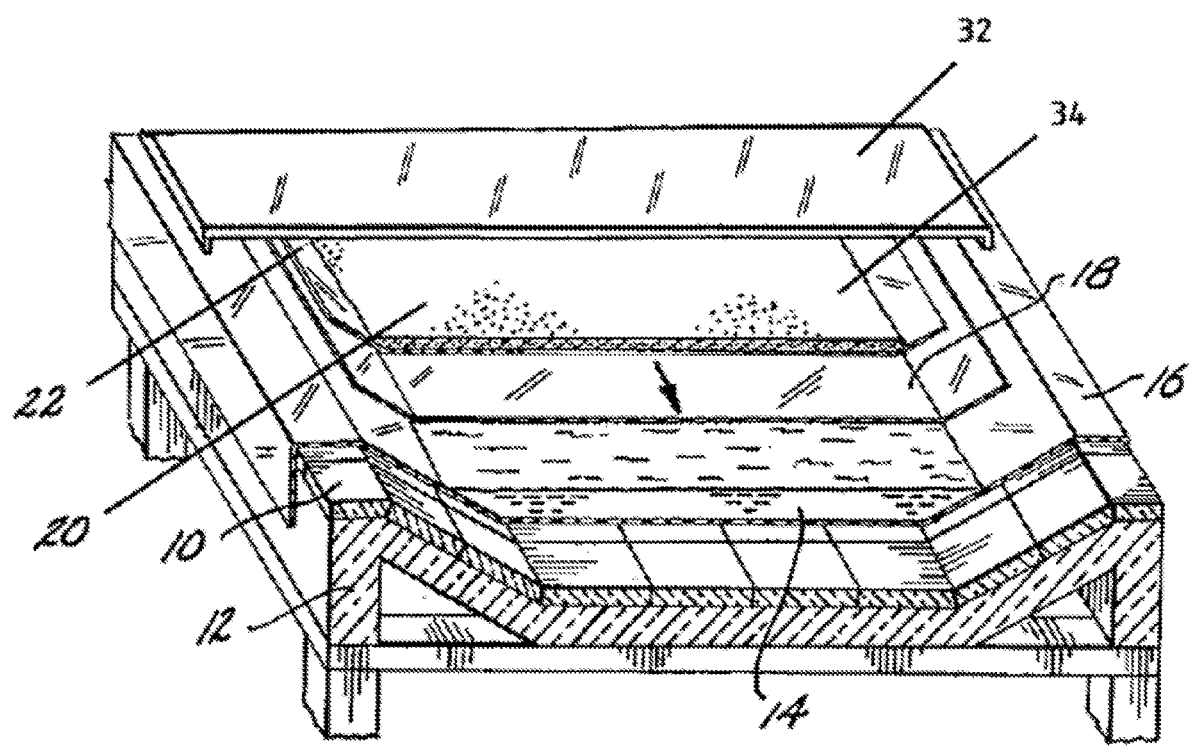
FIG. 2 is a perspective view of a drying apparatus, according to an embodiment of the present invention.

With reference to FIGS. 1 and 2, in an embodiment an apparatus 10 for the continuous production of a dry food supplement from edible type jellyfish is formed somewhat as an elongate trough 10*a*. The trough 10*a* is formed of some nonporous medium, such as ceramic tile or sheet metal carried on a supporting and generally insulating substrate or base 12. Heated and counter-flowing water is provided at the right end of the trough 10*a* (as seen in the drawing FIG. 1) via a pipeline 14*a*. This heated water 14 is pumped into the trough 10*a* from a source 15 of heated water, which may include an electric water heater, or a water heater fueled by any suitable fuel source, such as natural gas, wood, coal, etc. In practice, the heated water flows into the trough 10*a* at a first end which is at the right-hand end of the trough 10*a* as seen in drawing FIG. 1, and the trough is preferably slightly tilted along its length to be higher at the right-hand end so that the heated water runs by the force of gravity (see the water flow arrow on FIG. 1) to a second end of the trough 10*a*, which is the left-hand end as illustrated. From the left-hand end of the trough 10*a*, the now-cooler water is pumped back to the water heater 15 and is there reheated to the desired temperature. Thus, the water is re-used or is re-circulated, is re-heated, and it then pumped once again back into the trough 10*a* at the right-hand end so that the water in the trough is always maintained close to the predetermined, desired temperature. As will be further explained, however, the water flow is counter to the movement of jellyfish material along the trough 10*a*, so that the highest temperature water is exposed to the jellyfish matter, and the cooler water (i.e., cooled by passage along the length of trough 10*a*) is used to warm the initial temperature which the jellyfish matter is delivered onto the trough 10*a*.

In the illustrated embodiment, a sheet 16, which may preferably be made of polyethylene sheet material, lines the inner surface of the trough 10 and overhangs the edges of the trough to provide an additional moisture and heat barrier between the water and the trough. A flexible sheet of infrared-transparent, and substantially water-impermeable material 18 floats on the surface of the water 14 in the trough 10*a*. A suitable material has been found to be 300A Mylar, most preferably in a 3-mil-thick sheet. The 300A Mylar meets all of the requirements of the invention in that it shows very little distortion or shrinkage in the operable temperature range utilized in the machine 10. Further, this 300A material is flexible so that it lends itself to a conveyor belt type of application and also has the strength required to operate for long periods of time without breakage. While the polyester sheet 18 only needs to float on top of the water in the illustrated embodiment, the polyester sheet is wider than the trough 10 so that it not only overlies the water but also rides slightly up the sides of the trough 10a. The extra width of the polyester sheet 18 ensures a complete coverage of the water so that there is no evaporative exposure of the water to the open air above the trough. The overly-wide sheet 18 also provides a channel that keeps the jellyfish product to be dried 20 from running off of the polyester sheet into the hot water.

The moist jellyfish material 20, is placed in a thin layer on top of the polyester sheet 18 and remains on the polyester sheet until it reaches the proper consistency or dryness, that is, until a predetermined amount of the moisture is driven off the mixture by the heat transferred from the hot water to the jellyfish matter through the polyester sheet. It has been found that a thickness of approximately one-eighth to three-sixteenths of an inch, for the layer 20 of material to be dried, is capable of producing a satisfactory dried flake or mass of product. In the illustrated embodiment, a thin sheet 22 of material such as polyethylene, for example, 0.5 to 1.5 mils thick, is placed between the polyester sheet 18 and the jellyfish matter 20. The polyethylene sheet 22 does not enter directly into the workings of the process of the present invention, but, rather, supplies a convenient medium upon which to place the fruit pulp or other moist source material to prevent adherence of the jellyfish matter to the polyester sheet 18. The polyethylene sheet 22 is removed from the polyester sheet 18 with the dried jellyfish material to maintain the polyester sheet 18 in a clean condition for further processing and in suitable for use as a food supplement. Also, the polyethylene sheet separates easily from the Mylar sheet 18 so that the Mylar sheet is not damaged as it might be if it was necessary to scrape the dried fruit or vegetable pulp directly from the polyester sheet. The polyethylene sheet 22 and dried flake product can be removed simultaneously from the polyester sheet to provide a convenient method by which the dried product is transported for further processing (i.e., flaking, powdering, or granulizing) and/or stored after its removal from the dryer.

In one preferred form of the invention, the polyester sheet 18 is formed in an endless belt and is carried by a pair of rollers 24 and 26, respectively, mounted at either end of the trough 10a to form a conveyor belt. The moist jellyfish material 20 to be dried is introduced onto the polyester sheet at a first end of the trough from a discharge pipe 28 via a valve 28a. Most preferably, the discharge pipe 28 terminates in a spreader nozzle (not shown in the drawing Figures) having a width sufficient to place a wide thin ribbon of the moist jellyfish material on the sheet 22. The polyethylene sheet 22 is fed from a roll 30, also at the first end of the trough 10a, so that the jellyfish matter 20 lies on the polyethylene sheet 22. It is necessary to keep a slack in the polyester conveyor belt 18 so that the film floats on the water and is not under such tension that it resists contact with the water surface when the jellyfish material is placed on the belt.

Subsequently, the jellyfish material 20 moves over the counter-flowing hot water 14 on the polyester sheet conveyor belt 18 to the second end of the trough 10a. During this travel, the material 20 is warmed and gives up moisture. Conversely, the counter flowing water 14 is cooled. The speed of the conveyor belt is regulated so that the time that it takes for the jellyfish material to travel from one end of the trough 10a to the other is sufficient to produce the proper drying of the jellyfish material so that it can be removed along with the polyethylene sheet 22 at the second end of the trough 10a in the form of a dry flake or mass. Most preferably, the transit time for the jellyfish material and the length of the trough 10a are selected such that a dry flake or mass is provided at the right-hand end of the trough 10a. The polyester belt 18 returns to the left-hand end of the machine 10 under the trough 10a in a typical conveyor fashion, while the dried material is moved away on a second conveyor 32.

In one form of the invention, which has been tested, it has been found that jellyfish matter of one-eighth to three-sixteenths inch thickness placed on a Mylar sheet 3 mils thick over a trough of water in which the water depth is approximately one inch and the water is heated to just below the boiling point, that is, just below 100 degrees C., takes approximately at least two and one-half hours to dry to a suitable degree. Typically, the jellyfish material 20 may be open to the air during its drying. It may be thought that it would not be desirable to direct any heated or dried air onto the pulp as it dries because this may form an undesirable skin on the top of the material and impede drying by evaporation. This is the case unless the drying air flow stream is properly managed, as will be further explained. An air flow into and out of the room in which the dryer is located is certainly desirable to maintain the room air at a humidity that allows evaporation of the moisture in the jellyfish matter to the air and, in fact, dried heated air can be pumped into the room to lower the ambient humidity and increase the rate of absorption of water vapor by the air.

However, it has been found that in order to form a sufficiently dry flake type of product within a reasonable time interval and length for the trough 10a, that the jellyfish matter can be beneficially exposed to a dried and heated air flow, and especially to a confined counter-flow air flow. To this end, a cover 32 may be provided over substantially the entire length of the trough 10a, defining a captive air space 34 which opens to ambient at the left-hand end of the trough 10a, as will be further explained. A dryer 36 receives ambient air 36a, and dries this air (i.e., by desiccant or refrigeration process, for example). The dried air is then supplied to a heater 38 which heats the dry air to a controlled selected temperature, well above ambient, and possibly close to but less than boiling point of water. In an embodiment, the controlled selected temperature is 170 degrees Fahrenheit. In another embodiment, the controlled selected temperature is between 160 and 180 degrees Fahrenheit. This dried and heated air via duct 40 into the right hand end of the trough 10a in air space 34. Because of the counter flow of the dried and heated air, relative to the motion of the jellyfish material 20 (see the air flow arrow on FIG. 1), the tendency to form an undesirable dry crust on the surface of the product is reduced because the jellyfish product is first exposed (i.e., near the left-hand end of trough 10a) to a warm but humid drying air flow. This air flow has gained substantial humidity by passing along the length of trough 10a over the drying pulp product. So, drying of the jellyfish product at the left-hand end of the trough 10a is affected by a combination of warm water heating, and heating by warm air that is relatively high in humidity. On the other hand, as the drying product progresses toward the right (viewing FIG. 1) and approaches the right-hand end of the trough 10a, drying is affected by the warmest water in trough 10a in combination with the warmest and driest air in air space 34. Thus, a dry flake product is produced at the right-hand end of trough 10a, and is delivered onto conveyor 32, ready for further processing (such as placement in capsules or in bottles, for example).

Further to the above, it will be appreciated that the cover 32 is effective to shield the drying product below this cover from ultraviolet (UV) light. Such UV light could undesirably deteriorate or degrade some constituents of some food supplement products being processed according to this invention. Further, once the dried flake or jellyfish product is provided by the process at the right-hand end of machine 10 onto conveyor 32, efforts are preferably made to also protect the jellyfish product from exposure to UV light until the product is packaged in UV resistant packaging (i.e., in UV resistant bottles, for example).

In an embodiment, an apparatus described above with a water depth of at least one inch in the trough 10a, and with a trough of at least 12 meters in length, it has been found that the temperature drop of the water from the inlet at one end of the trough to the outlet from the trough is about 3 degrees C., or more. Therefore, the hot water source 15 does not have to expend much energy in raising the temperature of the water back to the desired temperature prior to reintroduction of the water into the trough 10a. The counter-flowing heated and dried air in air space 34, on the other hand, exits the machine 10 at 42 (see the air flow arrow on FIG. 1), and is now less warm but very moist (i.e., high in humidity) and is preferably captured by a vent hood (not seen in the drawing Figures) carrying this air of very high humidity outside of the processing environment.

It is important that the temperature of jellyfish matter 20 be kept below the boiling point so that there is no disruption or deterioration of the drying source material on the polyester sheet 18. And, this temperature restriction is very important for preservation of the natural nutrient values of the product. In an embodiment, the jellyfish material is kept at a temperature of between 70 and 90 degrees C. In another embodiment, the jellyfish material is held at a temperature between approximately 150 and 180 degrees Fahrenheit. The temperature also provides for sterilization of the jellyfish matter. In a preferred embodiment, the temperature is held at 170 degrees Fahrenheit. The water temperature should be kept below boiling in order to prevent bubbling and rapid evaporation of the water from the trough. The temperature of the heated and dried air introduced via duct 40 is also most preferably kept below the boiling point for water.

In an example method of drying jellyfish matter, a reservoir of water, such as in a trough, is heated to some predetermined temperature, preferably below the boiling point of water. A thin film of transparent material (i.e., transparent to heat or IR radiation), such as a polyester film, is floated on the water surface in the trough so that it covers substantially the entire open surface area of the water. Because of the floating contact of the film on the water surface and the film covering the water, there is little, if any, evaporation from the water to the air above it. Then, moist jellyfish material, to be dried, is placed on the film in heat-transfer contact with the surface of the water. The contact between the film carrying the product to be dried and the surface of the water enables a transfer of heat directly from the water through the film into the jellyfish product to be dried, causing the moisture in the product to be driven off. Additionally, a counter flow of dry, heated air may be provided above the product to be dried, assisting in producing a dry flake product. After the jellyfish product is dried to a consistency of a dry flake or mass, this product is then packaged in convenient forms for use as a food supplement. For example, the dry product may be placed in capsules, may be pressed into pill form, or may be placed loose in bottles.

In an embodiment, the moist jellyfish product is brought into heat-transfer relation (but not moisture-transfer relationship) with a heated water bath having a temperature close to but less than the boiling point for water.

In an embodiment, after the jellyfish product is brought into the heat-transfer relation, a progressive, slight increase in temperature (but still below the boiling point for water), begins with the temperature of the air flow stream increasing (but remaining below boiling) while the humidity becomes progressively dryer. This is continued until the moist pulp product to be dried becomes a dry flake or mass.

Figure 3A:
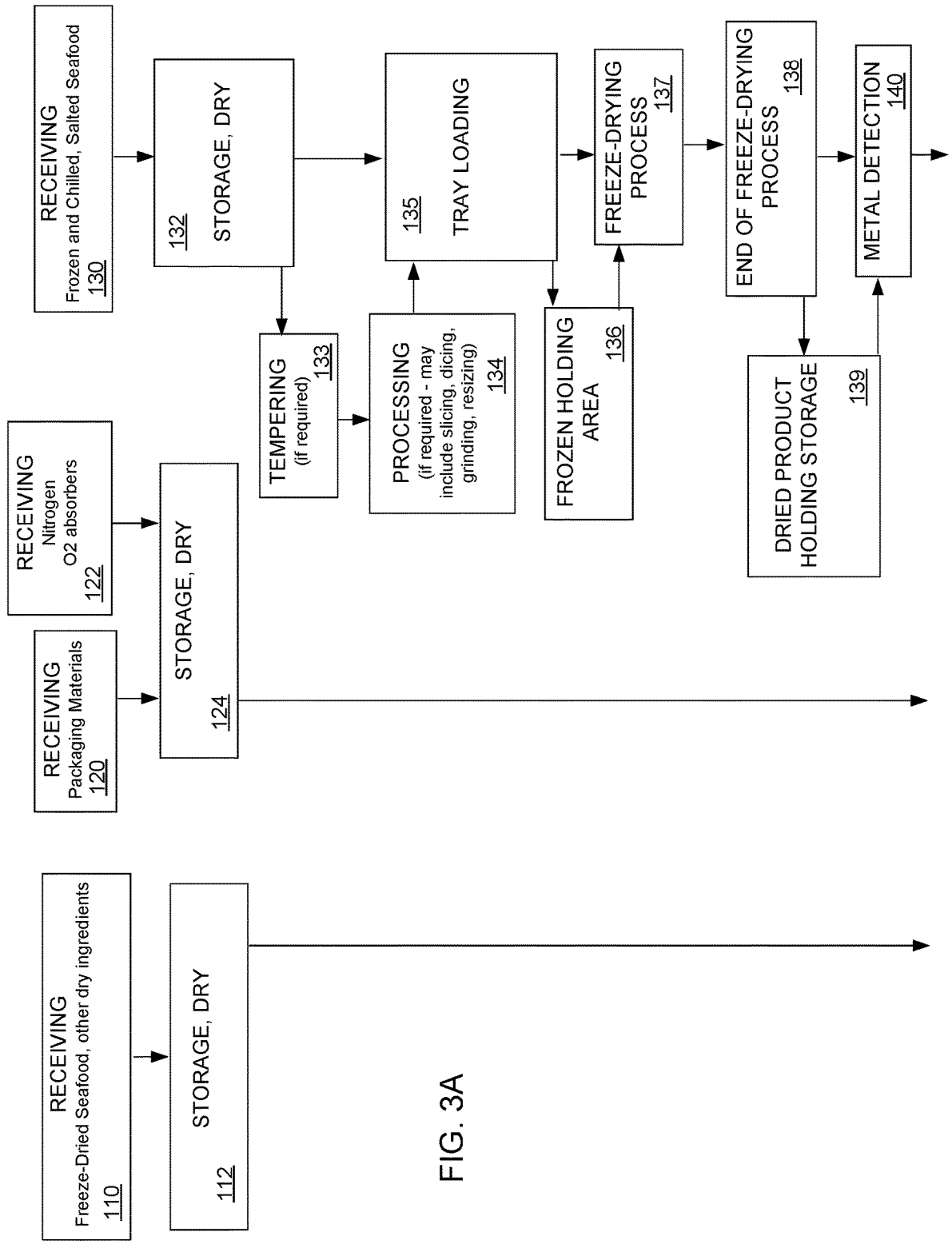
FIG. 3A is a diagram depicting the manufacturing of dried jellyfish collagen, according to an embodiment of the present invention.

With reference to FIG. 3A-3B, an embodiment of an overall manufacturing method for dried jellyfish product is depicted. In the embodiment, jellyfish product is received as freeze-dried at step 110. The freeze dried jellyfish matter is then stored in dry conditions at step 112 until it is ready to be processed.

In an embodiment, at step 130 jellyfish product is received in a frozen or chilled form. The frozen or chilled product is placed in frozen storage, at step 132, until it is selected to be processed. In an embodiment, the stored, frozen jellyfish material is tempered at step 133, if tempering is required. The tempered jellyfish material is then processed, if required, by slicing, grinding, dicing, resizing, etc. at step 134. The jellyfish product is then loaded into a tray loaded at step 135. If the product is not to be dried immediately, it is placed in a frozen holding area at step 136.

In an embodiment, at step 137 the product is freeze dried. In another embodiment, the jellyfish product is dried with another drying method disclosed herein. When the product is done being dried at step 138, it is held in storage at step 139. At step 140, the dried product is screened for any trace metallic particles before being packaged in bulk, at step 142, with packaging materials received at step 120. The packaging may also include nitrogen or oxygen absorbers received at step 122. Prior to step 150, the packaging materials are stored in a dry environment at step 124. In an embodiment, at step 144, the material packaged in bulk is resized and reprocessed as required by blending, sifting, screening, powdering, etc.

At step 148, the jellyfish matter is blended as required. In an embodiment, the jellyfish matter is then packaged at step 150 with packaging materials received at step 120. The packaging may also include nitrogen or oxygen absorbers received at step 122. Prior to step 150, the packaging materials are stored in a dry environment at step 124.

In an embodiment, the brite stock, or unlabeled product is help at step 154, until it is labeled at step 152. The final and labeled product is stored at step 146 until it is ready for distribution at step 170.

In an embodiment, a receiving customer or merchant begins a product check at step 160 when the dried jellyfish product is received. At step 162, the product is checked to see if the packaging is in a saleable condition. If not, the product is disposed of at step 164. If the product is in condition for sale, the original seal is checked at step 166. If the seal is broken the product is disposed of at step 164. If the seal is intact, then the product moves to the brite stock holding storage at step 154 (to be labeled) or to the finished product storage at step 146.

In an embodiment, wherein the product is freeze dried, the freeze drying (or lyophilization) process begins as the jellyfish matter is processed by slicing, grinding, dicing, resizing, etc. before being placed on trays, in vials, or in flasks to enter a freeze drying apparatus as part of a pretreatment phase. After pretreatment, the jellyfish matter begins the freezing stage. During the freezing process, the material is brought to below its triple point, where the solid, liquid, and gas phases of the jellyfish matter can coexist. To prevent formation of large ice crystals which can damage the structure of the jellyfish material, the jellyfish material is frozen rapidly. Rapid freezing lowers the material to below its eutectic point quickly to avoid formation of large ice crystals. In an embodiment, the eutectic point of the jellyfish material is approximately −21 degrees Celsius.

After the jellyfish material is frozen in the freeze dryer, the primary drying process begins. The pressure in the freeze dryer is lowered and enough heat is supplied to the material for the ice to sublime. In the primary drying phase, about 95% of the water in the material is sublimated. Pressure is controlled through the application of partial vacuum. The vacuum speeds up the sublimation, making it useful as a deliberate drying process. Furthermore, a cold condenser chamber and/or condenser plates provide a surface(s) for the water vapor to re-liquify on. In an embodiment, the primary drying of the product is considered complete when the temperature of the material is equal to the internal temperature of the freeze drying apparatus.

After completion of the primary drying process, the secondary drying process begins. The secondary drying phase aims to remove unfrozen water molecules, since the ice was removed in the primary drying phase. This part of the freeze-drying process is governed by the material's adsorption isotherms. In this phase, the temperature is raised higher than in the primary drying phase to break any physical/chemical interactions that have formed between the water molecules and the frozen material. The pressure can be lowered in this stage to encourage desorption After the freeze-drying process is complete, the vacuum is usually broken with an inert gas, such as nitrogen, before the material is sealed. In an embodiment, wherein vials are used for the jellyfish material, the vials may be backfilled and stoppered under a partial vacuum.

After the source material is dried to a consistency of a dry flaked or mass, it may be packaged in convenient forms and quantities for use as a food supplement. Importantly, because the product is never exposed to a processing temperature above that of boiling water, deterioration or important food values and nutrients in the jellyfish product does not occur. That is, the processing temperature is never made high enough to effect substantial oxidation or chemical alteration of the nutrients in the starting material. In the case of processing jellyfish product to produce a flake collagen product, the processing is carried out at a controlled low temperature such that the collagen protein does not react with water in the source material to product a hydrolyzed collagen product, and is subsequently desiccated by the drying process, as described above. Additionally, by greatly reducing the mass (i.e., the moisture content) of the jellyfish product source or starting material, the resulting food supplement may be consumed in a much smaller quantity to obtain the benefits of the jellyfish product than would be required if a person were to eat the equivalent amount of raw or cooked edible jellyfish.

When taken orally, research shown that hydrolyzed jellyfish collagen is beneficial in promoting brain function in age related neurological diseases. Oral administration may include oral, enteral, or intragastic administration. Several other research studies have shows benefits in reversing photo-aging, reducing fatigue, preventing arthritis, and reducing cell oxidation. Furthermore, the immune system is stimulated along with an increase in neurological activities. The targeted molecular weight range of 4 kilodaltons to 20 kilodaltons allows for the human body to easily assimilate the essential nutrient presents in the composition. In an embodiment, a dose would consist of about 500 to 1000 mg of the dried powder.

Type I collagen is the most abundant collagen in the human body. It is used in treating conditions of the bone and skin. Type II collagen is found in joint cartilage. Its oral ingestions appears to reduce autoimmunity resulting in reduced inflammation in instances of osteoarthritis and rheumatism. Other forms of connective tissue disorders have been greatly benefitted by type II collagen. Type V collagen has been associated with Ehlers-Danlos syndrome as well as other genetic and non-genetic connective tissue disorders. Various types of collagen have been found to reduce wrinkles, support re-growth of joint tissue, relieve joint pain, prevent osteoporosis, reduce cellulite, prevent stretch marks, aid in weight loss, detoxify the liver, repair leaky gut syndrome, support healthy hair growth, grow stronger nails, support healthy teeth, balance hormones, alleviate anxiety, promote restful sleep, prevent atherosclerosis, increase brain function, among many more benefits. Supplementing hydrolyzed collagen types I, II, and V can effectively be accomplished by oral ingestion or topical application depending on the desired result.

The composition may be taken as a nutritional supplement, prophylactic agent, or therapeutic. Oral administration may be accomplished by taking a powder, tablet, oil emulsion, aqueous or oil suspension, hard or soft capsule, syrup, tincture, or elixir. Each of these embodiments may be formed by a method known in the art for the manufacture of pharmaceutical, nutraceutical, or supplemental agents. The final product may contain artificial or natural sweeteners, flavoring agents, coloring agents, binding agents, thickening agents, emulsifiers, and preservatives. Any of these ingredients, and the combination thereof may increase the palatability of the composition. Binding agents may include starch, gelatin and acacia. Granulating and disintegrating agents may include corn starch and alginic acid. Lubricating agents may also be included including magnesium stearate, stearic acid, and talc. Furthermore, adjuvants as known in the art may be added to increase the bio-availability of the composition. Further, inert excipients may be used as known in the art. Excipients may include calcium carbonate, sodium carbonate, lactose, calcium phosphate, and sodium phosphate. If a tablet form is used, the tablets may be instantized, or time buffered by adjusting the coating of the tablet. Time buffering materials such as wax, glyceryl monostearate, or glyceryl distearate may be used. In further embodiment, enteric coatings may be used. In further embodiments, the composition may take forms as found in the cosmetic industry, such as facial creams, body lotions, lip sticks, and other skin topical treatments.

In oral use formulations, mixing the active ingredients of the composition with an inert solid diluent may produce hard capsules as known in the art. The inert solid diluent may include calcium carbonate, calcium phosphate, and kaolin. Soft gel formulations may include mixing the active ingredients of the composition with water or an oil medium.

Aqueous suspensions may be produced as known in the art through the utilization of suspending agents, dispersing agents, wetting agents, among others known in the art. Sweetening agents may be used as known in the art, including sucrose or saccharin.

Oil suspensions may be formulated by suspending the active ingredients of the composition in one or a combination of oils known in the art. Oil suspensions may contain a thickening agent such as waxes, hard paraffin, or cetyl alcohol. Oils used may be vegetable oil, coconut oil, arachis oil, mineral oil, or others.

Syrups and elixirs may be formulated with sweeting agents, demulcents, preservatives, flavoring agents, and coloring agents as known in the art.

Research studies show that ascorbic acid found in fruit juices promotes the formation of connective tissues when combined with hydrolyzed collagen powder. For this reason, a preferred embodiment involves combining the hydrolyzed collagen powder with an acid fruit juice prior to oral administration. Further, the fruit juice may be foregone by the user of powdered ascorbic acid mixed with the active ingredients of the composition in a tablet.

In a preferred embodiment, the active ingredients are formulated in one or more of the above-mentioned embodiments. The composition is administered orally as a nutritional supplement. The hydrolyzed collagen is administered at a daily dosage of 200 mg to 5000 mg. In a preferred embodiment, the effective daily dose is between 1500 mg and 2000 mg. In another preferred embodiment, the hydrolyzed collagen is taken on an empty stomach with a beverage containing ascorbic acid (vitamin C). In a preferred embodiment, the hydrolyzed collagen is mixed with the ascorbic acid containing beverage prior to administration of the mixture.

The invention has been described herein using specific embodiments for the purposes of illustration only. It will be readily apparent to one of ordinary skill in the art, however, that the principles of the invention can be embodied in other ways. Therefore, the invention should not be regarded as being limited in scope to the specific embodiments disclosed herein, but instead as being fully commensurate in scope with the following claims.

I claim:

1. A method for freeze-drying a moist jellyfish material comprising the steps of:
    pre-processing the moist jellyfish material;
    loading the moist jellyfish material into one or more drying containers;
    placing the one or more drying containers into a freeze-drying apparatus;
    lowering the temperature of the freeze-drying apparatus to below the eutectic point of the moist jellyfish material;
    applying a vacuum to the freeze-drying apparatus;
    increasing an internal temperature of the freeze-drying apparatus;
    holding the internal temperature of the freeze-drying apparatus;
    increasing the internal temperature of the freeze-drying apparatus;
    holding the internal temperature of the freeze-drying apparatus;
    removing the vacuum from the freeze-drying apparatus;
    allowing the internal temperature of the freeze-drying apparatus to reach room temperature, and
    removing dried jellyfish material from the freeze-drying apparatus and grinding the dried jellyfish material into a powder.

2. The method of claim 1, wherein step of removing the vacuum from the freeze-drying apparatus further comprises introducing an inert gas into the freeze-drying apparatus.

3. The method of claim 2, wherein the inert gas consists of nitrogen, argon, or a combination thereof.

4. The method of claim 1, wherein the eutectic point of the jellyfish material is approximately −21 degrees Celsius.

* * * * *